United States Patent
Jogasaki et al.

(10) Patent No.: US 10,343,291 B2
(45) Date of Patent: Jul. 9, 2019

(54) GRIPPING MECHANISM AND GRIPPER

(71) Applicant: OLYMPUS CORPORATION, Tokyo (JP)

(72) Inventors: Shuya Jogasaki, Tokyo (JP); Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/191,543

(22) Filed: Nov. 15, 2018

(65) Prior Publication Data

US 2019/0077026 A1    Mar. 14, 2019

Related U.S. Application Data

(63) Continuation of application No. PCT/JP2016/065962, filed on May 31, 2016.

(51) Int. Cl.
  *B25J 15/02*    (2006.01)
  *A61B 17/29*    (2006.01)
  *B25J 15/08*    (2006.01)

(52) U.S. Cl.
  CPC .......... *B25J 15/0233* (2013.01); *A61B 17/29* (2013.01); *B25J 15/08* (2013.01); *A61B 2017/2902* (2013.01); *A61B 2017/2939* (2013.01)

(58) Field of Classification Search
  CPC ........ B25J 15/0233; B25J 15/08; A61B 17/29
  USPC ................................. 294/200, 106
  See application file for complete search history.

(56) References Cited

U.S. PATENT DOCUMENTS

| 6,206,903 | B1 | 3/2001 | Ramans |
| 6,896,704 | B1 | 5/2005 | Higuchi et al. |
| 8,821,480 | B2* | 9/2014 | Burbank ................ A61B 34/71 606/1 |
| 8,936,289 | B1* | 1/2015 | Kozlowski ........... B25J 15/0009 294/106 |
| 9,615,846 | B2* | 4/2017 | Prestel ................... A61B 17/29 |

(Continued)

FOREIGN PATENT DOCUMENTS

| EP | 1 195 151 A1 | 4/2002 |
| EP | 1 854 418 A1 | 11/2007 |

(Continued)

OTHER PUBLICATIONS

International Search Report dated Aug. 9, 2016 issued in International Application No. PCT/JP2016/065962.

*Primary Examiner* — Paul T Chin

(74) *Attorney, Agent, or Firm* — Scully, Scott, Murphy & Presser, P.C.

(57) ABSTRACT

A gripping mechanism according to the present invention is provided with: two gripping pieces pivoted about a pivoting axis; a gripper main body that supports the gripping pieces at a distal-end portion; a pulley that is supported about a rotation axis that is parallel to the pivoting axis; an opening wire that is wound around the pulley that has one end secured to the gripping pieces or the gripper main body, and that causes tensile forces that cause the rotation axis to be moved in one direction pulley, wherein the pulley is disposed so that a resultant force of the tensile forces in the opening wire that acts on the rotation axis becomes greater than the pulling force, and so that a moment that causes the gripping pieces to be pivoted in the directions in which the gripping pieces are opened relative to each other is generated.

11 Claims, 17 Drawing Sheets

(56) References Cited

U.S. PATENT DOCUMENTS

| | | | |
|---|---|---|---|
| 2002/0040217 A1 | 4/2002 | Jinno | |
| 2004/0267406 A1 | 12/2004 | Jinno | |
| 2006/0167589 A1 | 7/2006 | Jinno | |
| 2007/0288044 A1 | 12/2007 | Jinno et al. | |
| 2008/0232932 A1 | 9/2008 | Jinno | |
| 2010/0259057 A1* | 10/2010 | Madhani | B25J 9/1045 294/106 |
| 2012/0239011 A1 | 9/2012 | Hyodo et al. | |
| 2013/0110289 A1* | 5/2013 | Cho | B25J 13/085 700/258 |
| 2018/0050456 A1 | 2/2018 | Yamanaka | |

FOREIGN PATENT DOCUMENTS

| | | |
|---|---|---|
| EP | 2 666 429 A1 | 11/2013 |
| JP | 2000-325375 A | 11/2000 |
| JP | 2002-102248 A | 4/2002 |
| JP | 2007-301692 A | 11/2007 |
| JP | 2012-187311 A | 10/2012 |
| WO | 2016/194777 A1 | 12/2016 |

\* cited by examiner

GRIPPING MECHANISM AND GRIPPER

CROSS-REFERENCE TO RELATED APPLICATIONS

This is a continuation of International Application PCT/JP2016/065962, with an international filing date of May 31, 2016, which is hereby incorporated by reference herein in its entirety.

TECHNICAL FIELD

The present invention relates to a gripping mechanism and a gripper.

BACKGROUND ART

In the related art, there is a known gripping mechanism with which an object such as living tissue is gripped by using a pair of gripping pieces that are joined in a pivotable manner, wherein a toggling mechanism is utilized (for example, see Japanese Unexamined Patent Application, Publication No. 2007-301692). The toggling mechanism is provided with a pair of linkages that are joined so as to be pivotable about a pivoting axis shared with the pair of gripping pieces, and an opening motion of the pair of linkages is converted to a closing motion of the pair of gripping pieces. In this structure, it is possible to increase the gripping force exerted by the pair of gripping pieces in accordance with the lengths of the pair of linkages.

SUMMARY OF INVENTION

A first aspect of the present invention is a gripping mechanism comprising: two gripping pieces that are pivoted relative to each other about a pivoting axis; a gripper main body that supports at least one of the gripping pieces so as to pivot at a distal-end portion thereof; a pulley that is supported so as to rotate about a rotation axis that is parallel to the pivoting axis; and an opening wire that is wound around the pulley, that has one end thereof secured to one of the gripping pieces or the gripper main body, and that causes, with a pulling force applied to the other end thereof, tensile forces that cause the rotation axis to be moved in one direction to act on two sides of the pulley, with the rotation axis being interposed therebetween, wherein the pulley is disposed so that a resultant force of the tensile forces in the opening wire that acts on the rotation axis becomes greater than the pulling force, and so that a moment that causes the gripping pieces to be pivoted in the directions in which the gripping pieces are opened relative to each other is generated.

Another aspect of the present invention is a gripping mechanism comprising: two gripping pieces that are pivoted about a pivoting axis relative to each other; a gripper main body that supports at least one of the gripping pieces so as to pivot at a distal-end portion thereof; a first pulley and a second pulley that are supported so as to individually rotate about a first rotation axis and a second rotation axis that are parallel to the pivoting axis; an opening wire that is wound around the first pulley, that has one end thereof secured to one of the gripping pieces or the gripper main body, and that causes, with a first pulling force applied to the other end thereof, tensile forces that cause the first rotation axis to be moved in one direction to act on two sides of the first pulley, with the first rotation axis being interposed therebetween; and a closing wire that is wound around the second pulley, that has one end thereof secured to the gripper main body, and that causes, with a second pulling force applied to the other end thereof, tensile forces that cause the second rotation axis to be moved in the other direction to act on two sides of the second pulley, with the second rotation axis being interposed therebetween, wherein the first pulley is disposed so that a resultant force of the tensile forces in the opening wire that act on the first rotation axis becomes greater than the first pulling force, and so that a moment that causes the gripping pieces to be pivoted in the directions in which the gripping pieces are opened relative to each other is generated, and the second pulley is disposed so that a resultant force of the tensile forces in the opening wire that acts on the second rotation axis becomes greater than the second pulling force, and so that a moment that causes the gripping pieces to be pivoted in the directions in which the gripping pieces are closed relative to each other is generated.

Another aspect of the present invention is a gripper provided with: any one of the above-described gripping mechanisms; and a driving portion that is connected to the gripping mechanism and that is configured to generate the pulling force.

DESCRIPTION OF EMBODIMENTS

A gripping mechanism 3 and a gripper 1 provided with the gripping mechanism 3, according to a first embodiment of the present invention, will be described below with reference to the drawings.

Figure 1:
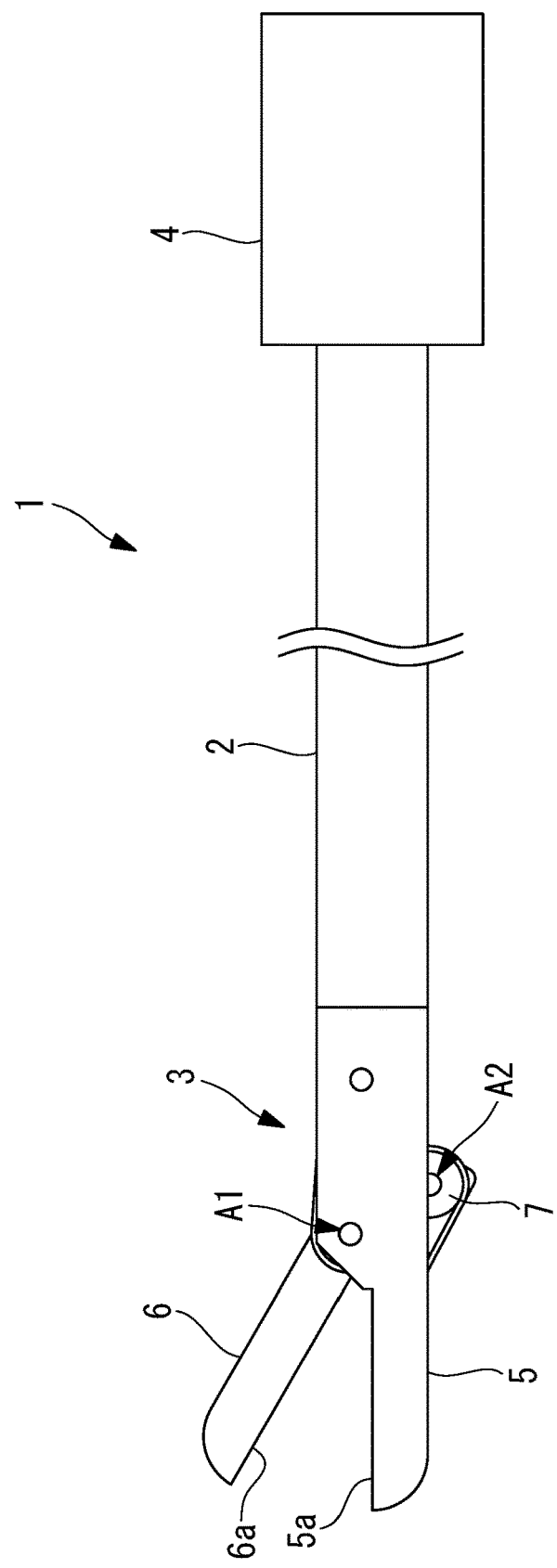
FIG. 1 is an overall configuration diagram of a gripper according to an embodiment of the present invention.

The gripper 1 according to this embodiment is medical equipment that is used when treating living tissue. As shown in FIG. 1, the gripper 1 is provided with: a long, thin body portion (gripper main body) 2 that can be inserted into a body; a gripping mechanism 3 that is provided at a distal end of the body portion 2, and a driving portion 4 that is connected to a proximal end of the body portion 2.

Figure 2:
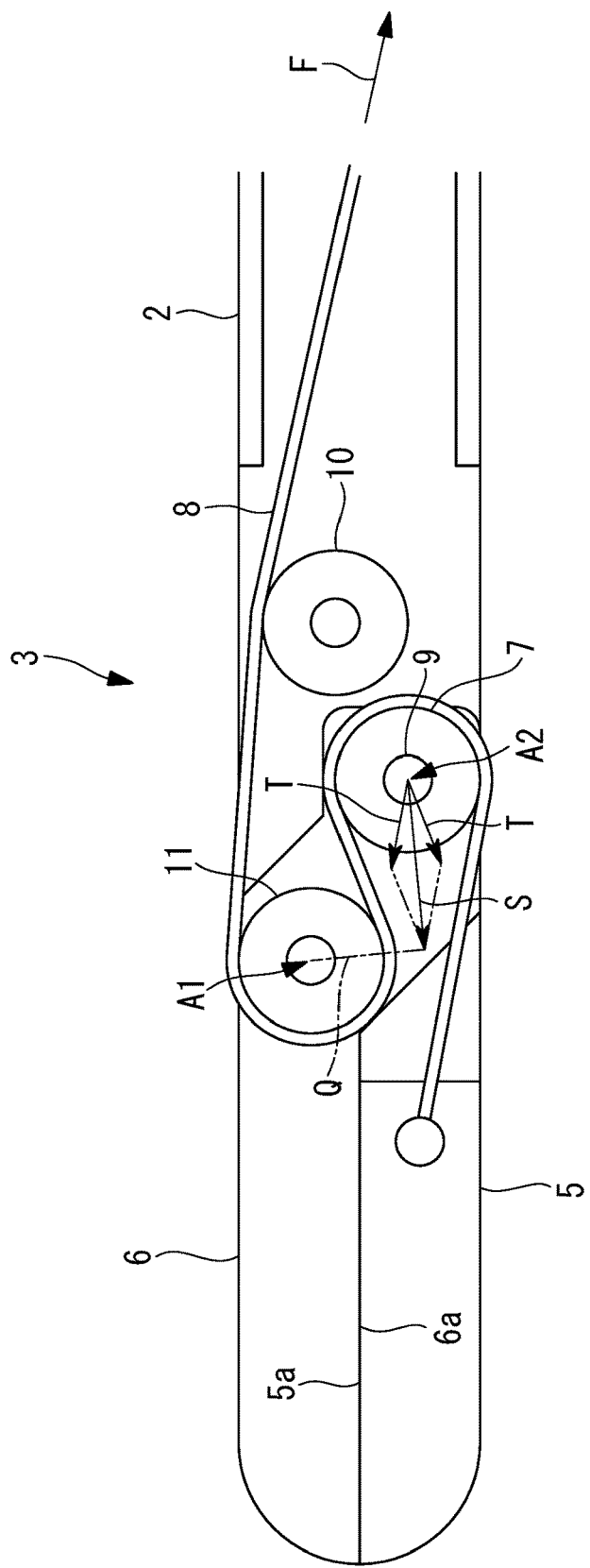
FIG. 2 is a longitudinal cross-sectional view showing a state in which two gripping pieces of a gripping mechanism according to a first embodiment of the present invention are closed.
Figure 3:
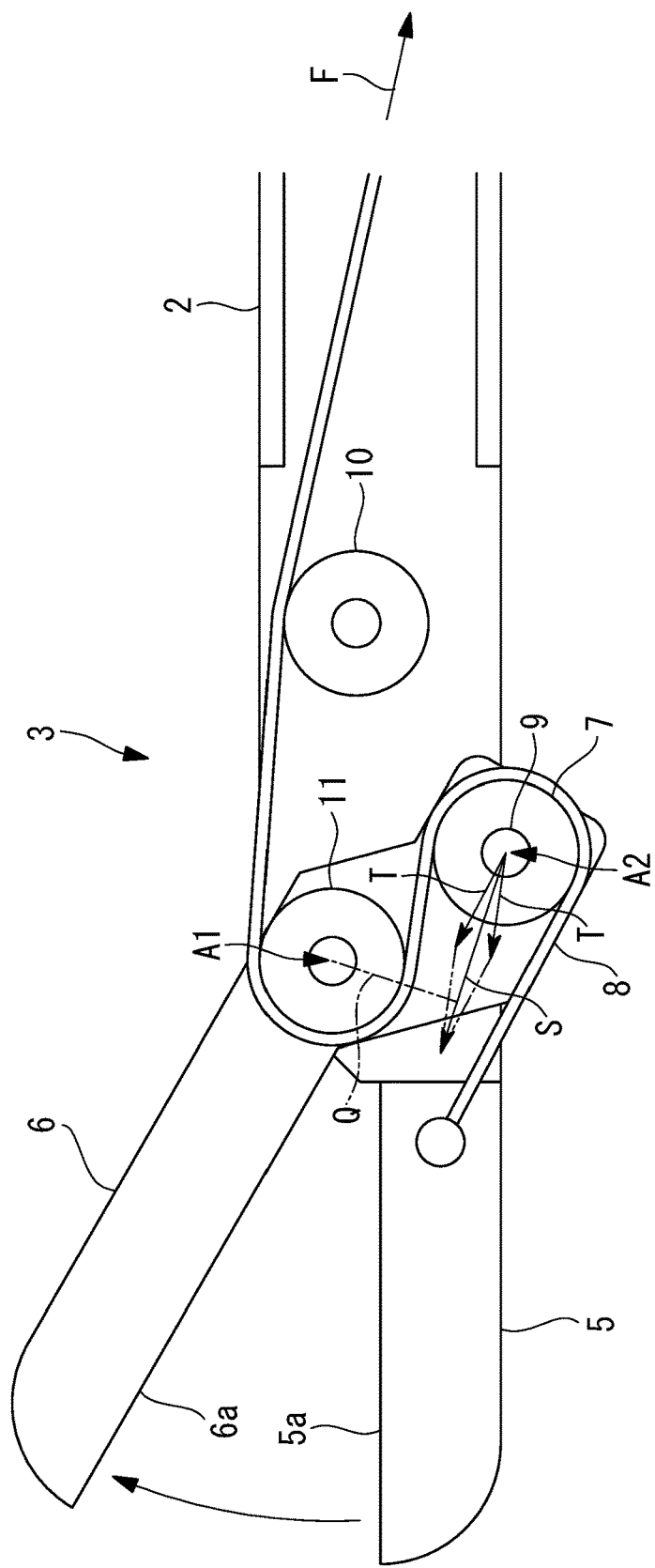
FIG. 3 is a longitudinal cross-sectional view showing a state in which the two gripping pieces of the gripping mechanism in FIG. 2 are open.

As shown in FIGS. 2 and 3, the gripping mechanism 3 according to this embodiment is provided with: a first gripping piece 5 that is secured to the body portion 2; a second gripping piece 6 that is joined with the first gripping piece 5 so as to be pivotable about a pivoting axis A1 that is orthogonal to the longitudinal axis of the body portion 2; a pulley 7 that is supported by the second gripping piece 6 so as to be rotatable about a rotation axis A2 that is parallel to the pivoting axis A1; and a wire 8 that is wound around the pulley 7. FIG. 2 shows a closed state in which the second gripping piece 6 is closed with respect to the first gripping piece 5. In the figures, reference sign 10 is an idler.

The first gripping piece 5 has a first gripping surface 5a on a distal-end side thereof, and the second gripping piece 6 has a second gripping surface 6a on a distal-end side thereof. The first gripping piece 5 and the second gripping piece 6 are individually disposed in directions along the longitudinal direction of the body portion 2 so that the gripping surfaces 5a and 6a face each other.

The pivoting axis A1 that connects the second gripping piece 6 to the first gripping piece 5 in a pivotable manner is disposed farther on the proximal-end side than the first gripping surface 5a and the second gripping surface 6a are. As a result of the second gripping piece 6 pivoting about the pivoting axis A1, the distal ends of the first gripping piece 5 and second gripping piece 6 are opened/closed.

The pulley 7 is supported, in a rotatable manner, by a shaft 9, which is co-axial with the rotation axis A2 of the pulley 7, farther on the proximal-end side than the pivoting axis A1 of the second gripping piece 6 is.

The pivoting axis A1 supports a return pulley (return portion) 11 so as to be pivotable about the pivoting axis A1.

The wire 8 is disposed inside the body portion 2 in the longitudinal direction thereof, and a distal-end portion thereof is folded back as a result of being wound substantially half way around the return pulley 11 on an outer circumferential surface on a distal-end side thereof, and is secured to the distal end of the first gripping piece 5 farther on the distal-end side than the pivoting axis A1 is after being wound approximately half way around the pulley 7 on an outer circumferential surface on a proximal-end side thereof. The proximal end of the wire 8 is connected to the driving portion 4.

The portions of the wire 8 that are wound substantially half way around the pulley 7 and that extend in two tangential directions of the pulley 7 are disposed so as to be substantially parallel to each other. As shown in FIG. 2, center line between the two portions the wire 8 that are substantially parallel to each other are disposed with a spacing therebetween in the direction that is orthogonal to the pivoting axis A1.

The driving portion 4 has a motor (not shown) to which the proximal end of the wired 8 is connected, and a tensile force is generated in the wire 8 by pulling the wire 8 toward the proximal end by operating the motor.

The operations of the thus-configured gripping mechanism 3 and gripper 1 according to this embodiment will be described below.

With the gripper 1 according to this embodiment, as a result of the wire 8 being pulled toward the proximal end by operating the driving portion 4, tensile forces that are substantially equal to a pulling force F are generated in the individual portions of the wire 8.

Because substantially equal tensile forces T are also individually generated in the two portions of the wire 8 that are disposed on the two sides of the rotation axis A2 of the pulley 7, a resultant force S of these tensile forces T acts on the rotation axis A2 of the pulley 7 in the directions along the center line between the two portions of the wire 8, as shown in FIG. 2. Because the center line between the two portions of the wire 8 is disposed with a spacing with respect to the pivoting axis A1, and the rotation axis A2 is secured to the second gripping piece 6, a moment that is proportional to the length of a perpendicular line Q drawn to the center line from the pivoting axis A1 and the magnitude of the resultant force S acts on the second gripping piece 6.

In the example shown in FIGS. 2 and 3, a clockwise moment acts on the second gripping piece 6, the second gripping piece 6 is pivoted clockwise about the pivoting axis A1 with respect to the first gripping piece 5, and thus, the gripping surfaces 5a and 6a are opened with respect to each other. By doing so, with the first gripping piece 5 and the second gripping piece 6 that are inserted between pieces of tissue in a state in which the first gripping piece 5 and the second gripping piece 6 are closed with the gripping surfaces 5a and 6a in close contact, as shown in FIG. 2, it is possible to increase the spacing between the pieces of tissue by opening the first gripping piece 5 and the second gripping piece 6 with respect to each other, as shown in FIG. 3.

In this case, with the gripping mechanism 3 according to this embodiment, because the resultant force S of the two tensile forces T that are directed substantially in the same direction acts on the pulley 7, it is possible to pivot the second gripping piece 6 with a force that is amplified substantially twofold relative to the pulling force F applied to the proximal end of the wire 8. In other words, even in the case in which a small pulling force F is applied to the proximal end of the wire 8, it is possible to increase the spacing between the pieces of tissue with a large force.

Comparing FIG. 2 and FIG. 3, the length of the perpendicular line Q drawn from the pivoting axis A1 to the center line between the two portions of the wire 8 wound around the pulley 7 is greater in FIG. 3. In other words, because the moment that is proportional to the length of the perpendicular line Q increases as the second gripping piece 6 is increasingly opened with respect to the first gripping piece 5, there is an advantage in that it is possible to more easily increase the spacing between the pieces of tissue with respect to each other.

With this embodiment, because the wire 8 is folded back by the return pulley 11, it is possible to facilitate guiding the proximal end of the wire 8 toward the proximal end of the long, thin body portion 2 of the gripper 1, and there is an advantage in that it is possible to reduce the diameter of the gripper 1.

In this embodiment, because the two portions of the wire 8 that are wound around the pulley 7 are disposed so as to be substantially parallel to each other, it is possible to cause a force that is twice as great as the pulling force F exerted on the wire 8 to act on the pulley 7; however, there is no limitation thereto. In other words, because the resultant force S of the tensile forces T becomes equal to the pulling force F when the relative angle of the two portions of the wire 8 is 120°, there is an advantage in that it is possible to amplify the pulling force F so long as the two portions of the wire 8 form an angle that is less than 120°. However, in order to achieve the long, thin shape of the gripper 1, it is preferable that the two portions of the wire 8 be disposed so as to be close to substantially parallel to each other.

Next, a gripping mechanism 13 according to a second embodiment of the present invention will be described below with reference to the drawings.

In describing this embodiment, portions having the same configurations as the gripping mechanism 3 according to the first embodiment, described above, will be given the same reference signs, and descriptions thereof will be omitted.

The gripping mechanism 13 according to this embodiment is provided with: a first elongated hole 14 that is provided in the first gripping piece 5 secured to the distal end of the body portion 2, that has a depth in the direction that is parallel to the pivoting axis A1, and that linearly extends in a direction that substantially connects the distal end and the proximal end; and a second elongated hole 15 that is provided in the second gripping piece 6, that has a depth in the direction that is parallel to the pivoting axis A1, and that linearly extends, in an inclined manner, in the direction that intersects the first elongated hole 14.

The shaft 9 that extends along the rotation axis A2 of the pulley 7 is disposed so as to pass through the first elongated hole 14 and the second elongated hole 15, and the pulley 7 is supported so as to be movable in the longitudinal direction of the first elongated hole 14 and the second elongated hole 15.

The return pulley 11 is provided at the pivoting axis A1 so as to be coaxially rotatable.

Figure 4:
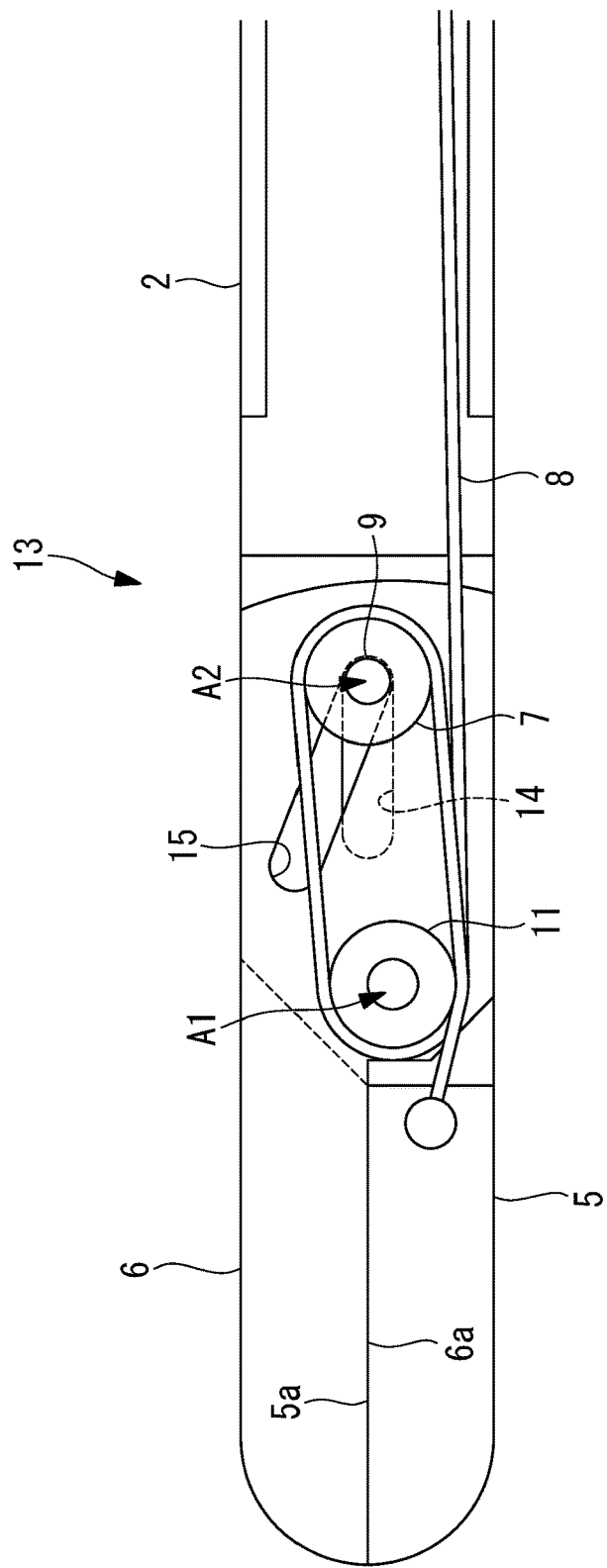
FIG. 4 is a longitudinal cross-sectional view showing a state in which two gripping pieces of a gripping mechanism according to a second embodiment of the present invention are closed.

In the example shown in FIG. 4, the wire 8 extending from the proximal-end side of the body portion 2 is wound clockwise substantially half way around the return pulley 11, and is secured to the first gripping piece 5 farther on the distal-end side than the pivoting axis A1 is after also being wound clockwise substantially half way around the pulley 7.

The operation of the thus-configured gripping mechanism 13 according to this embodiment will be described below.

With the gripping mechanism 13 according to this embodiment, when the pulling force F is applied to the proximal-end side of the wire 8, the tensile forces that are substantially equal to the pulling force F are generated in the individual portions of the wire 8. By doing so, a resultant force S that is substantially twice as great as the pulling force F and that is directed toward the distal end acts on the rotation axis A2 of the pulley 7.

Figure 5:
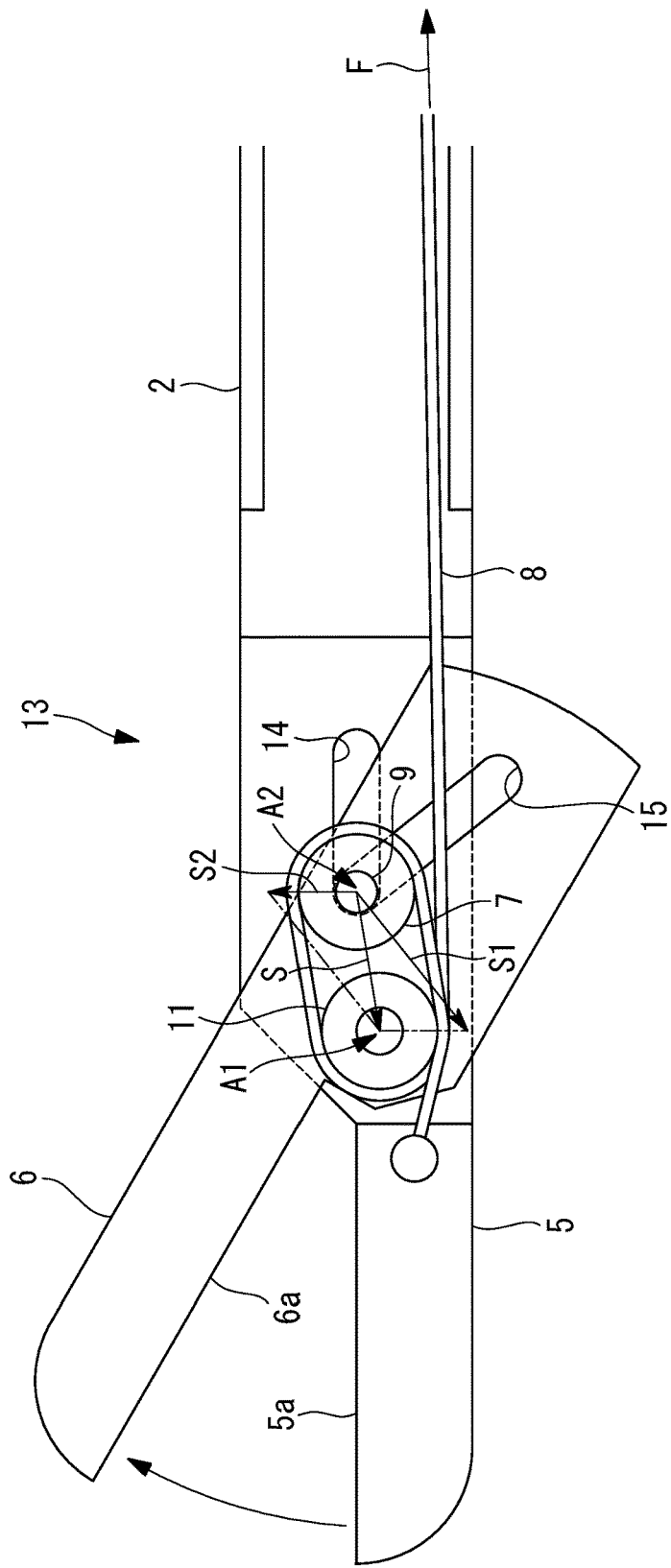
FIG. 5 is a longitudinal cross-sectional view showing a state in which the two gripping pieces of the gripping mechanism in FIG. 4 are open.

Because the rotation axis A2 of the pulley 7 is inserted into the two elongated holes 14 and 15 so as to be movable in the longitudinal directions of the elongated holes 14 and 15, as shown in FIG. 5, the resultant force S that has acted on the rotation axis A2 is decomposed into resultant-force components S1 and S2 that are individually directed in the directions that are orthogonal to the two elongated holes 14 ad 15, and the resultant-force component S1 generates a moment that causes the second gripping piece 6 to be pivoted clockwise about the pivoting axis A1. By doing so, the second gripping piece 6 is opened with respect to the first gripping piece 5, as shown in FIG. 5.

In other words, also with the gripping mechanism 13 according to this embodiment, it is possible to generate a large moment by the resultant force S that is amplified to a magnitude that is greater than that of the pulling force F applied to the proximal end of the wire 8, and to cause the first gripping piece 5 and the second gripping piece 6 to be pivoted in the directions in which the first gripping piece 5 and the second gripping piece 6 are opened with respect to each other.

Figure 6:
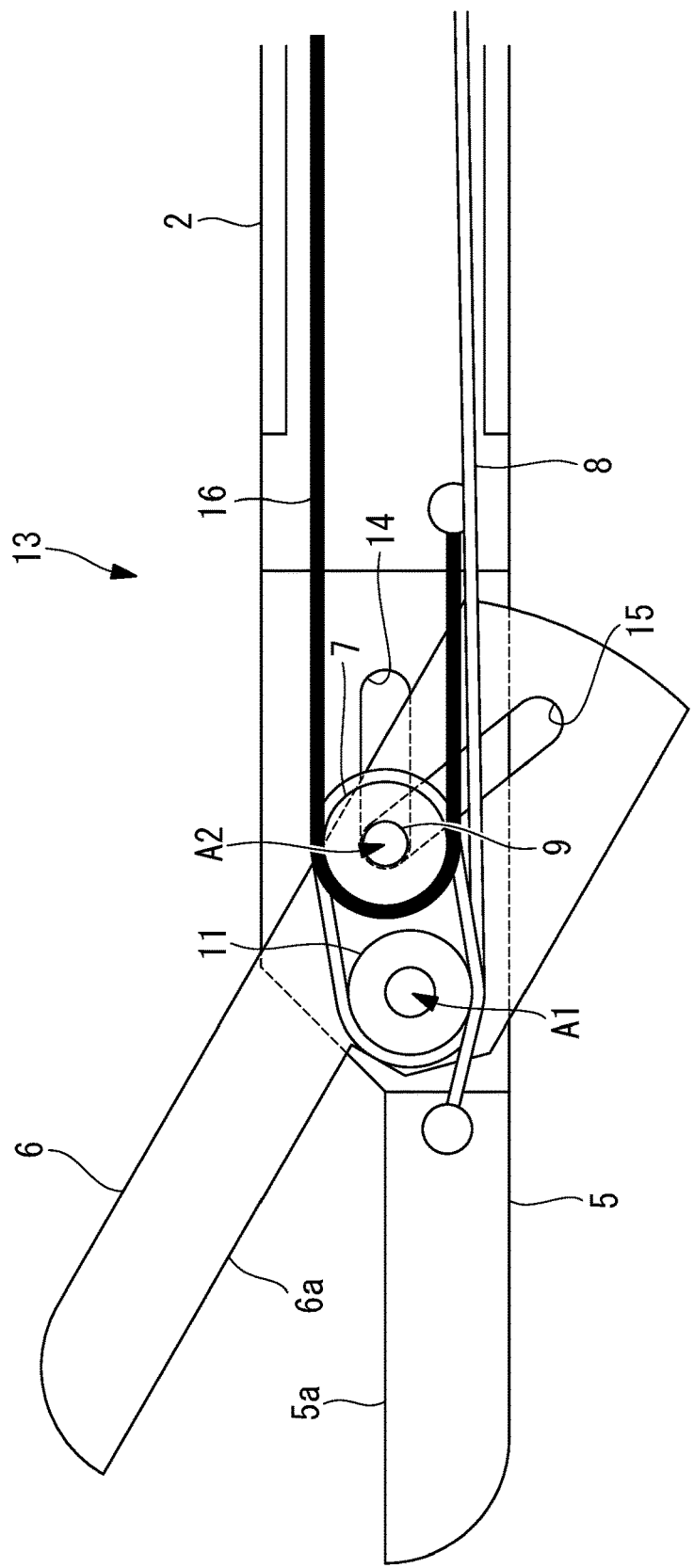
FIG. 6 is a longitudinal cross-sectional view showing a state in which two gripping pieces of a modification of the gripping mechanism in FIG. 4 are open.
Figure 7:
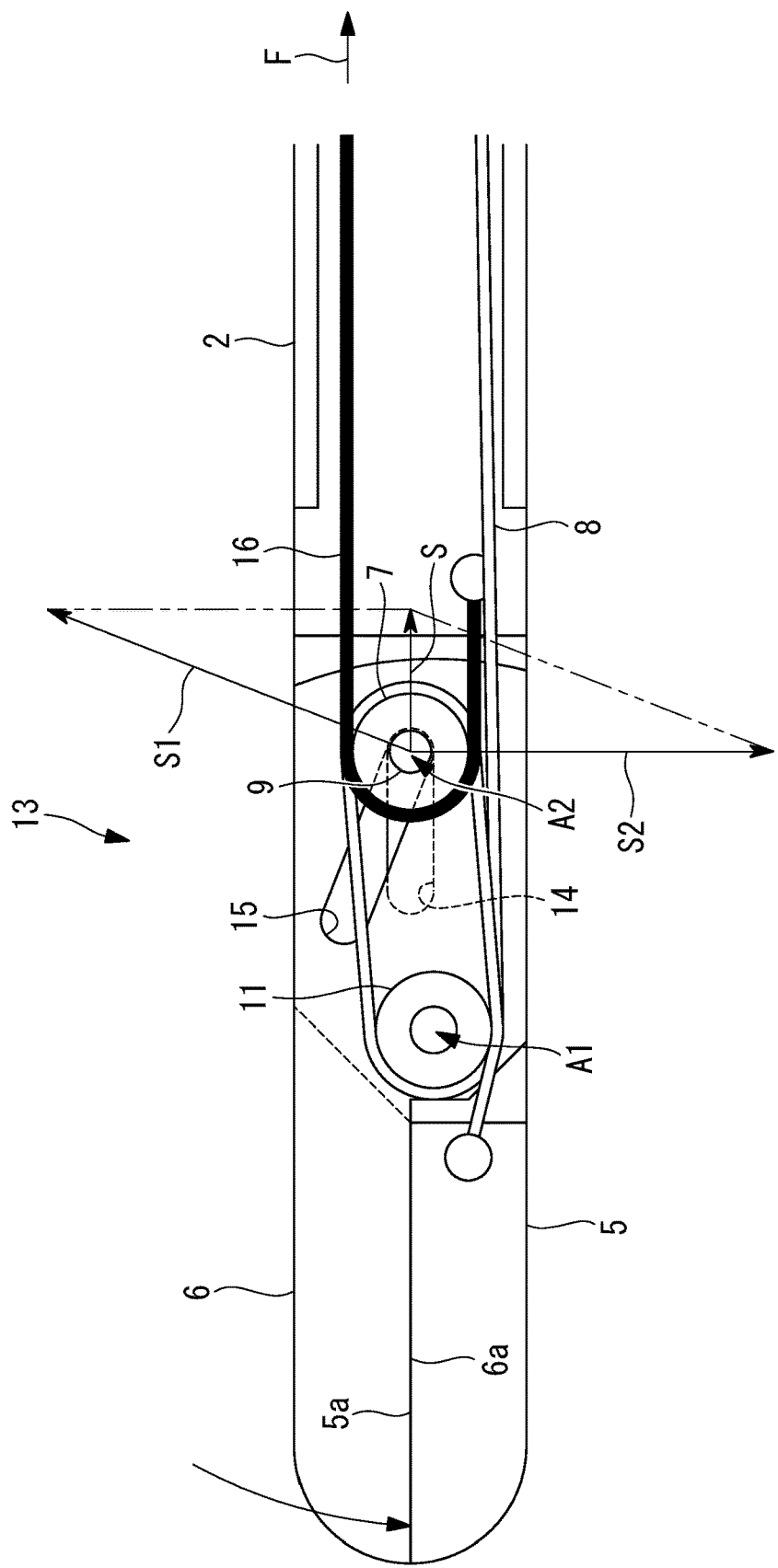
FIG. 7 is a longitudinal cross-sectional view showing a state in which the two gripping pieces of the gripping mechanism in FIG. 6 are closed.

In this embodiment, as shown in filled lines in FIGS. 6 and 7, another wire (closing wire) 16 may be wound around the pulley 7, and a distal end of the wire 16 may be secured to the body portion 2. As a result of moving the pulley 7 toward the proximal end by canceling the pulling force F exerted on the wire 8 and by causing the pulling force F to act on the proximal end of the wire 16 instead, it is possible to cause the second gripping piece 6 to be pivoted counter-clockwise about the pivoting axis A1 with respect to the first gripping piece 5, and to bring the gripping surfaces 5a and 6a close to each other.

In this case, by also winding the wire 16 substantially half way around the pulley 7, it is possible to pull the pulley 7 toward the proximal end with the resultant force S that is approximately twice as great as the pulling force (closing pulling force) F applied to the proximal end of the wire 16, and thus, there is an advantage in that, by generating a large moment with the resultant-force component S1, it is possible to firmly grip tissue or the like between the first gripping piece 5 and the second gripping piece 6 with a small pulling force F.

Next, a gripping mechanism 20 according to a third embodiment of the present invention will be described below with reference to the drawings.

In describing this embodiment, portions having the same configurations as the gripping mechanism 13 according to the second embodiment, described above, will be given the same reference signs, and descriptions thereof will be omitted.

As shown in FIGS. 8-11, in the gripping mechanism 20 according to this embodiment, elongated holes (a second elongated hole 21 and a third elongated hole 22) having depths in the longitudinal direction of the pivoting axis A1 are individually formed from both sides of the second gripping piece 6 in the longitudinal direction of the pivoting axis A1. The second elongated hole 21 and the third elongated hole 22 are individually provided so as to be inclined in opposite directions from each other with respect to the elongated hole (first elongated hole) 14 that is provided in the first gripping piece 5 along the front-to-rear direction.

Figure 8:
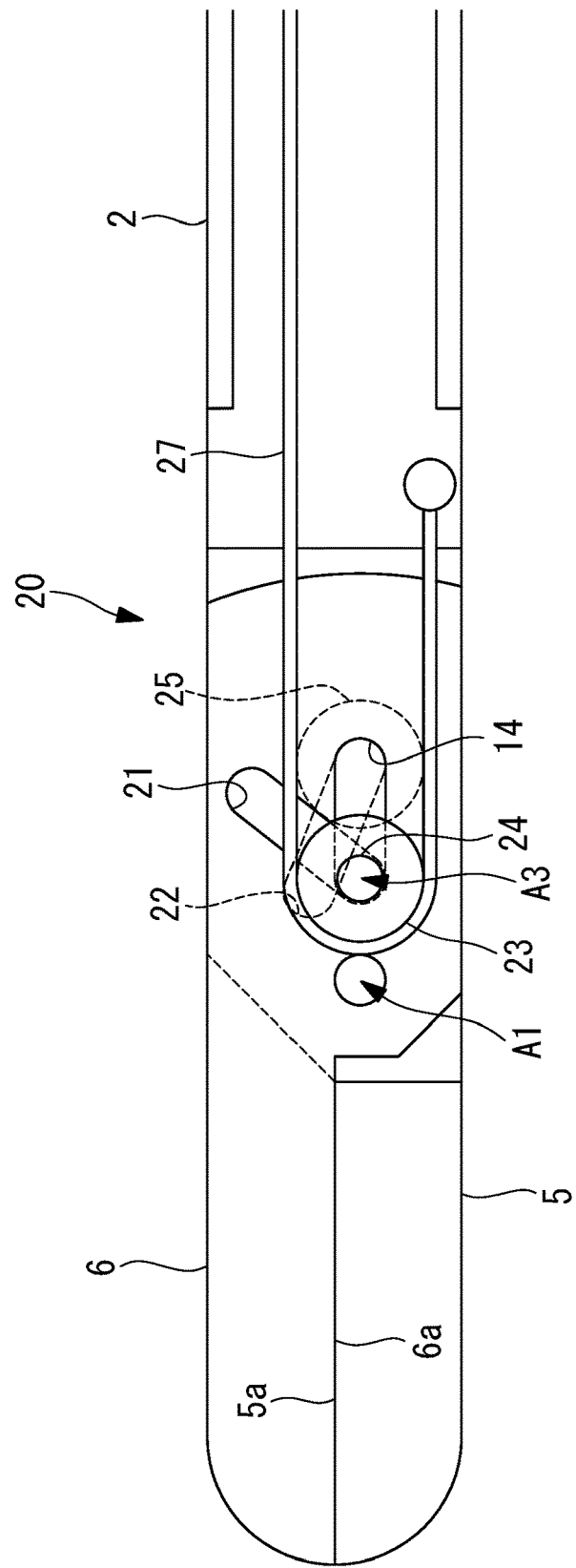
FIG. 8 is a longitudinal cross-sectional view showing a state in which two gripping pieces of a gripping mechanism according to a third embodiment of the present invention are closed.
Figure 9:
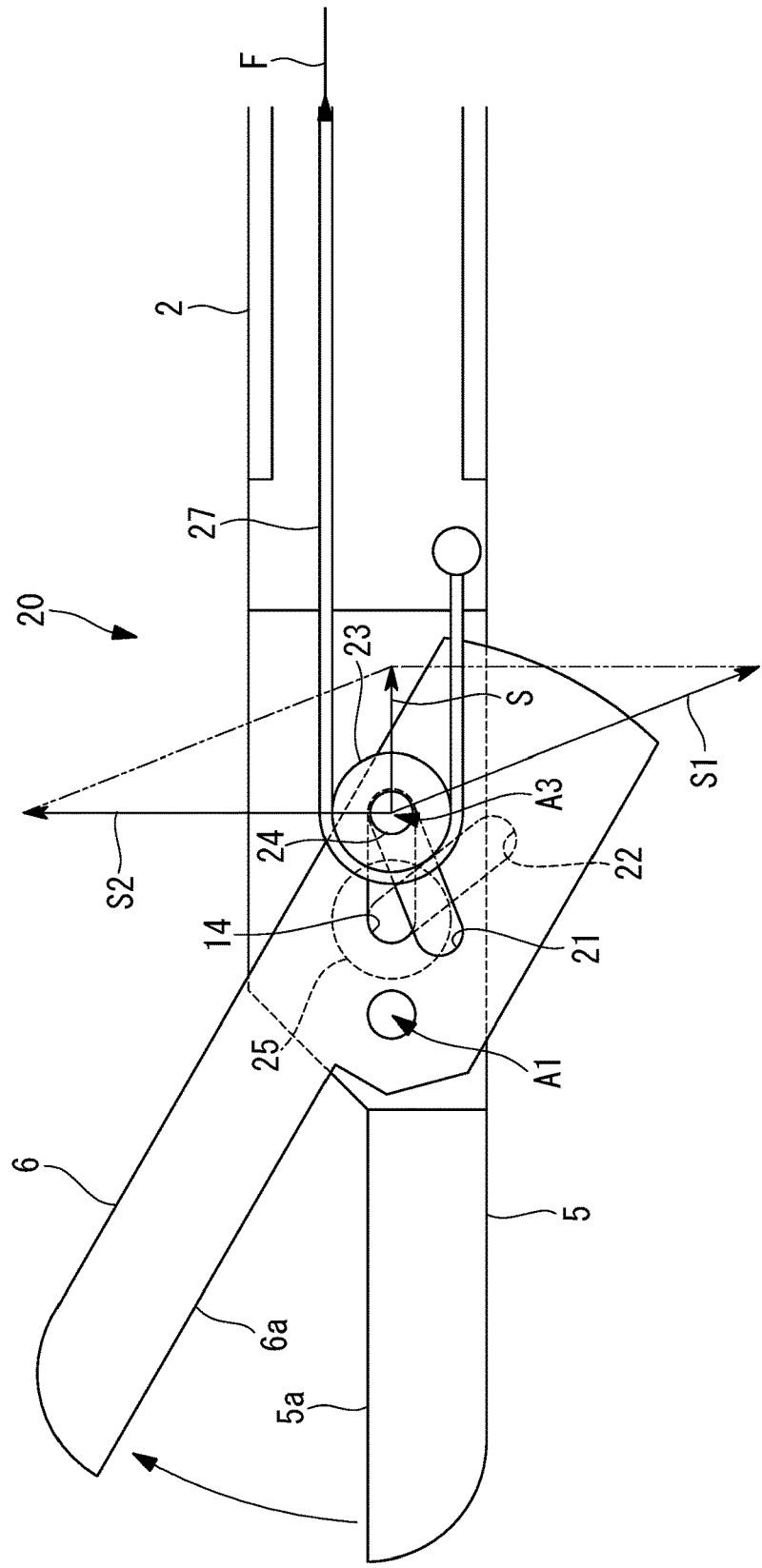
FIG. 9 is a longitudinal cross-sectional view showing a state in which the two gripping pieces are opened by manipulating an opening wire of the gripping mechanism in FIG. 8.

As shown in FIGS. 8 and 9, a shaft 24 that includes a first rotation axis A3 of the first pulley 23 is inserted at a position at which the second elongated hole 21 on one side of the second gripping piece 6 and the first elongated hole 14 of the first gripping piece 5 intersect each other.

Figure 10:
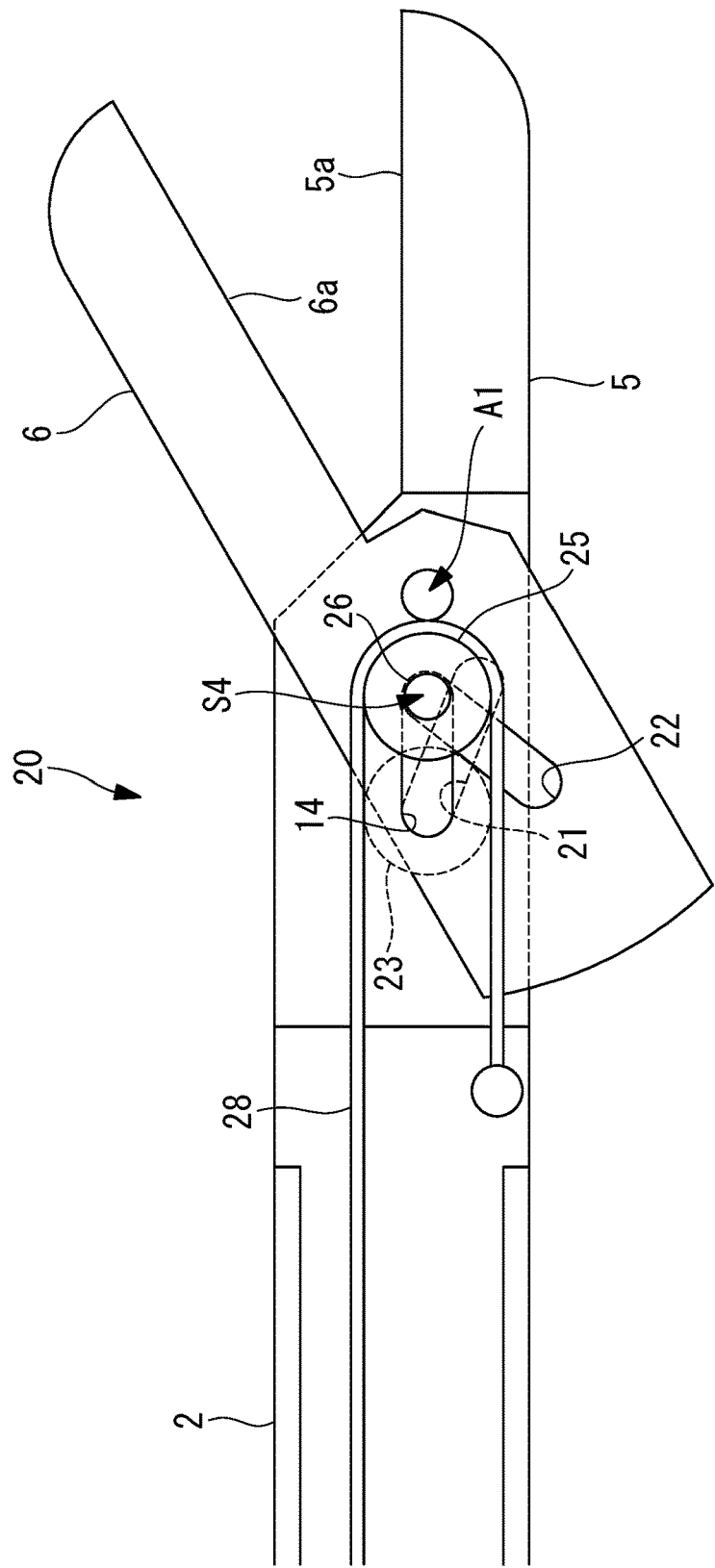
FIG. 10 is a longitudinal cross-sectional view in which the gripping mechanism in FIG. 9 is viewed from an opposite side.
Figure 11:
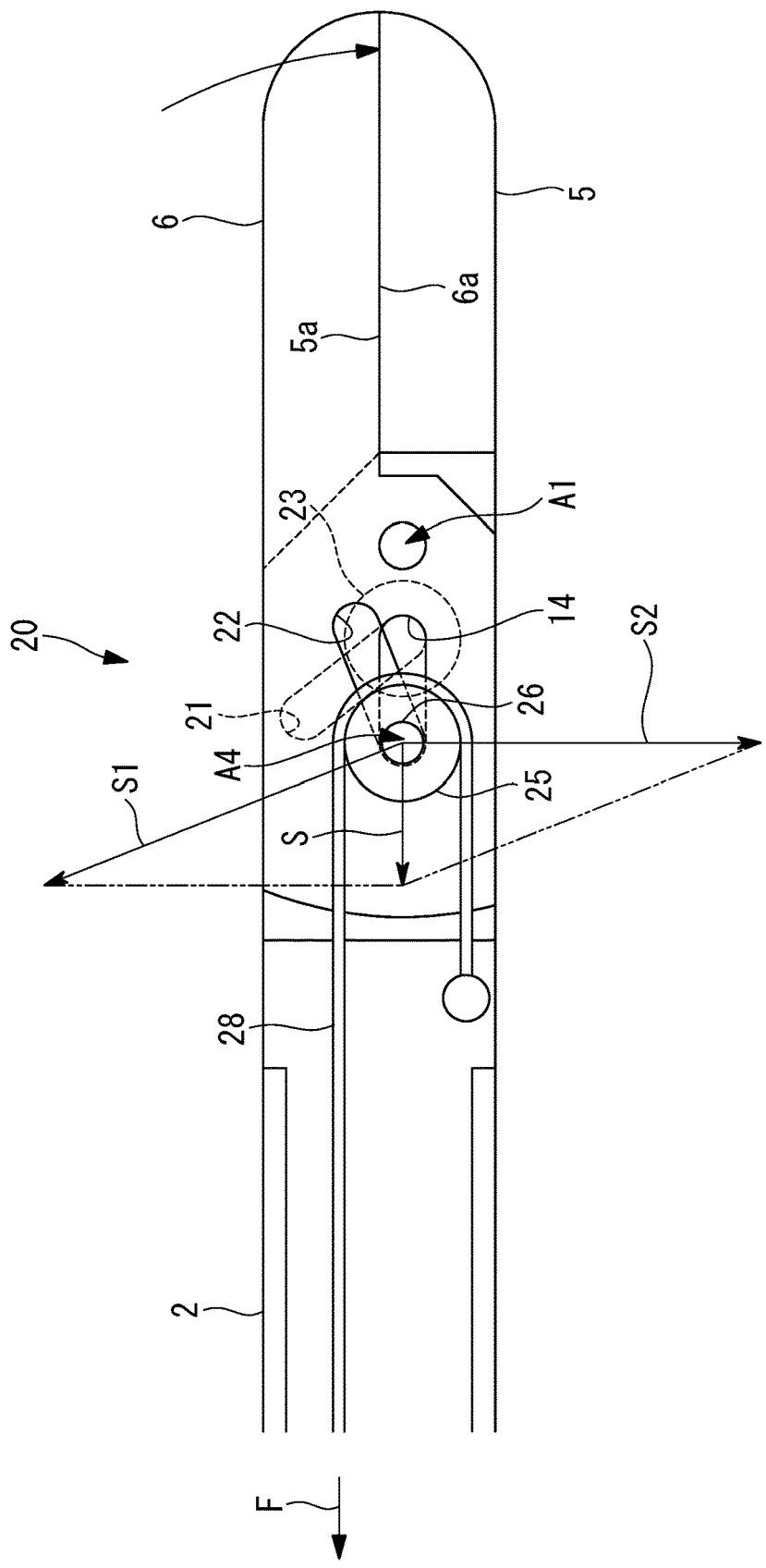
FIG. 11 is a longitudinal cross-sectional view showing a state in which the two gripping pieces are closed by manipulating a closing wire of the gripping mechanism in FIG. 10.

On the other hand, as shown in FIGS. 10 and 11, a shaft 26 that includes a second rotation axis A4 of the second pulley 25 is inserted at a position at which the third elongated hole 22 on the other side of the second gripping piece 6 and the first elongated hole 14 intersect each other.

As shown in FIGS. 8 and 9, an opening wire 27 that causes the second gripping piece 6 to be pivoted in the opening direction with a pulling force F applied to a proximal end thereof is wound around the first pulley 23. As shown in FIGS. 10 and 11, a closing wire 28 that causes the second gripping piece 6 be pivoted in the closing direction with the pulling force F applied to a proximal end thereof is wound around the second pulley 25.

Because a resultant force S that is twice as great as the pulling forces F acts on each of the first rotation axis A3 of the first pulley 23 and the second rotation axis A4 of the second pulley 25, there is an advantage in that, just by applying small pulling forces F, it is possible to open/close the second gripping piece 6 with respect to the first gripping piece 5 with a large resultant-force component S1.

Figure 12:
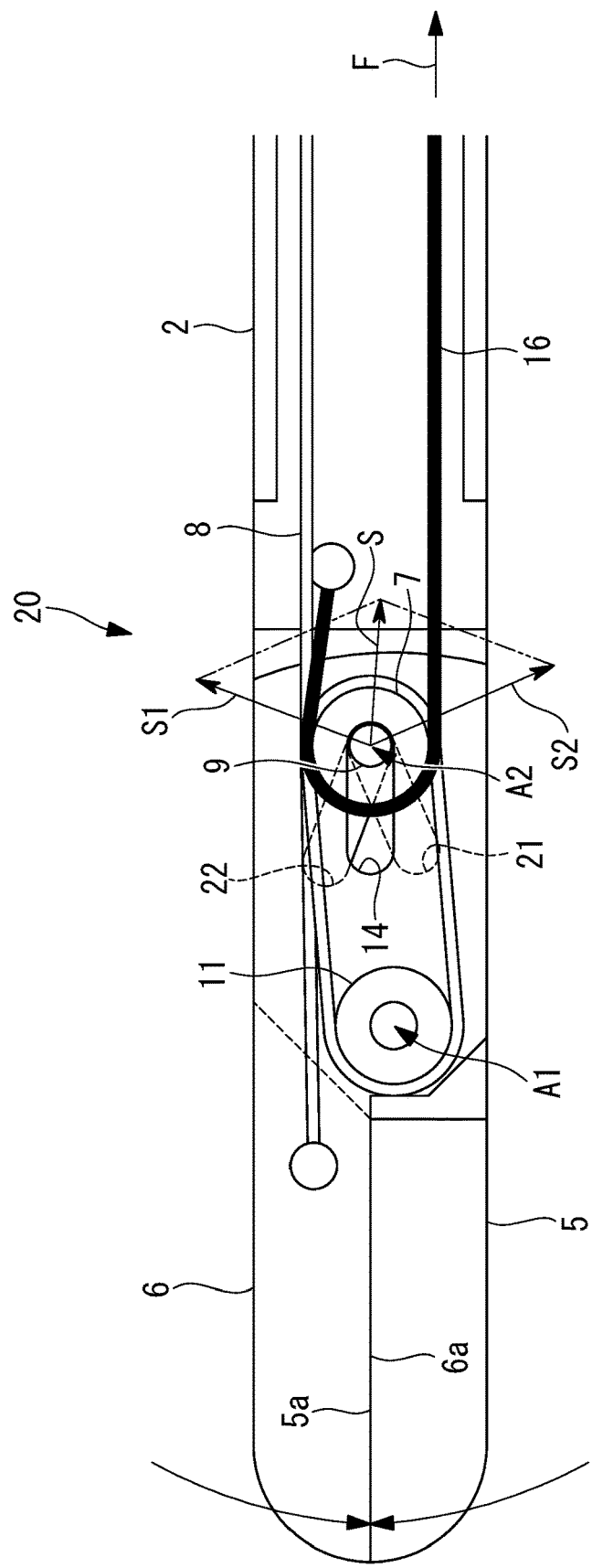
FIG. 12 is a longitudinal cross-sectional view showing a state in which two gripping pieces of a modification of the gripping mechanism in FIG. 9 are closed.
Figure 13:
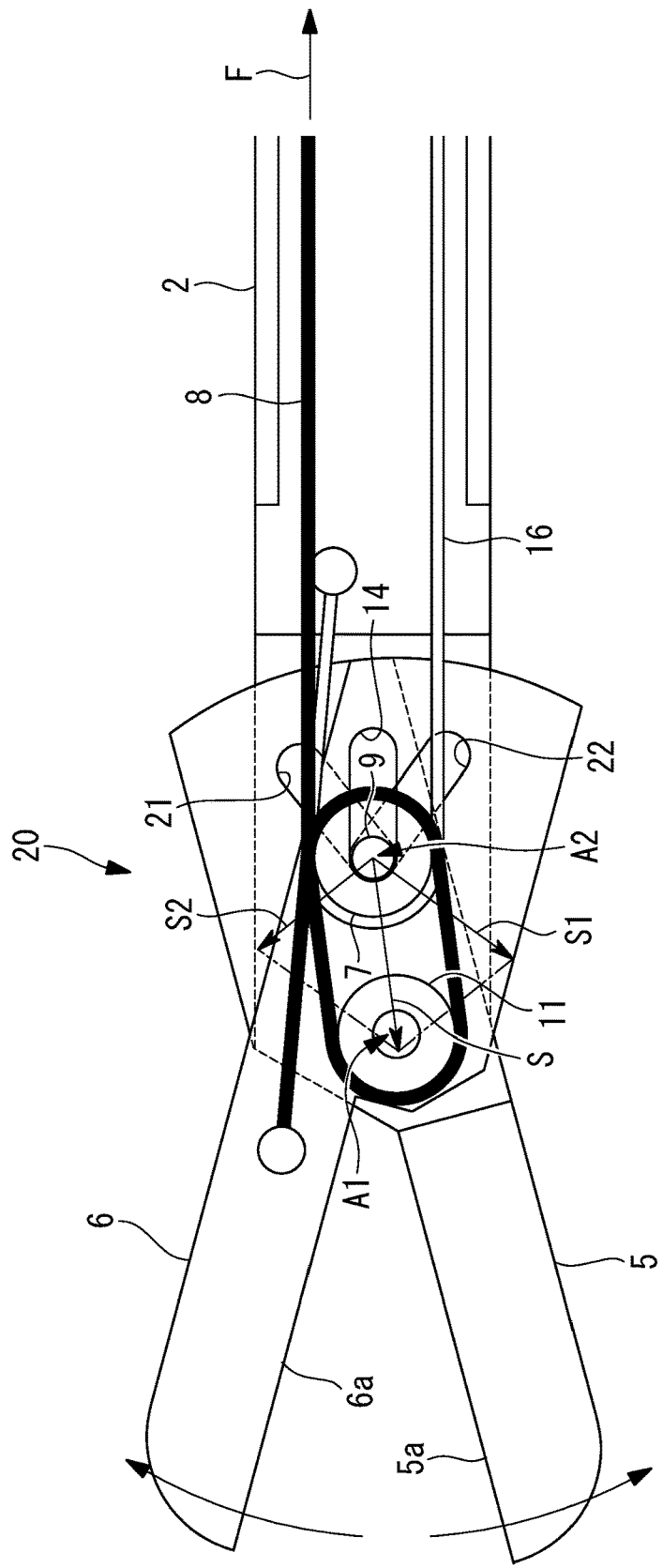
FIG. 13 is a longitudinal cross-sectional view showing a state in which the two gripping pieces of the gripping mechanism in FIG. 12 are open.

In this embodiment, the second elongated hole 21 and the third elongated hole 22 that are inclined in opposite directions are provided in the second gripping piece 6, and the opening operation and the closing operation are separately performed by the two pulleys 23 and 25; however, alternatively, as shown in FIGS. 12 and 13, both the first gripping piece 5 and the second gripping piece 6 may be supported at the distal end of the body portion 2 so as to be pivotable about the shared pivoting axis A1.

In this case, by providing the second elongated hole 21 in the first gripping piece 5 and by providing the third elongated hole 22 in the second gripping piece 6, the first gripping piece 5 and the second gripping piece 6 may be pivoted in the directions in which the first gripping piece 5 and the second gripping piece 6 are opened with respect to each other by moving the pulley 7 toward the distal end by means of the wire 8, as shown in FIG. 13, and the first gripping piece 5 and the second gripping piece 6 may be pivoted in the directions in which the first gripping piece 5 and the second gripping piece 6 are closed with respect to each other by moving the pulley 7 toward the proximal end by means of the wire 16, as shown in FIG. 12.

Figure 14:
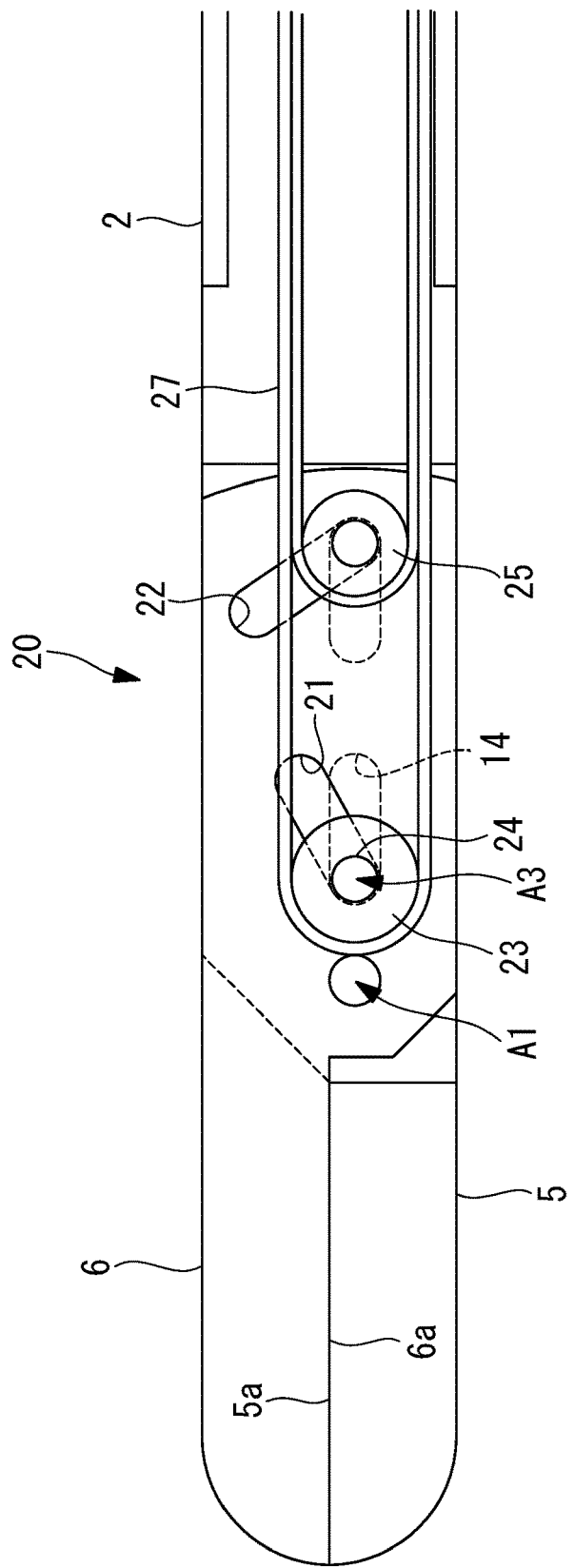
FIG. 14 is a longitudinal cross-sectional view showing a state in which two gripping pieces of another modification of the gripping mechanism in FIG. 9 are closed.
Figure 15:
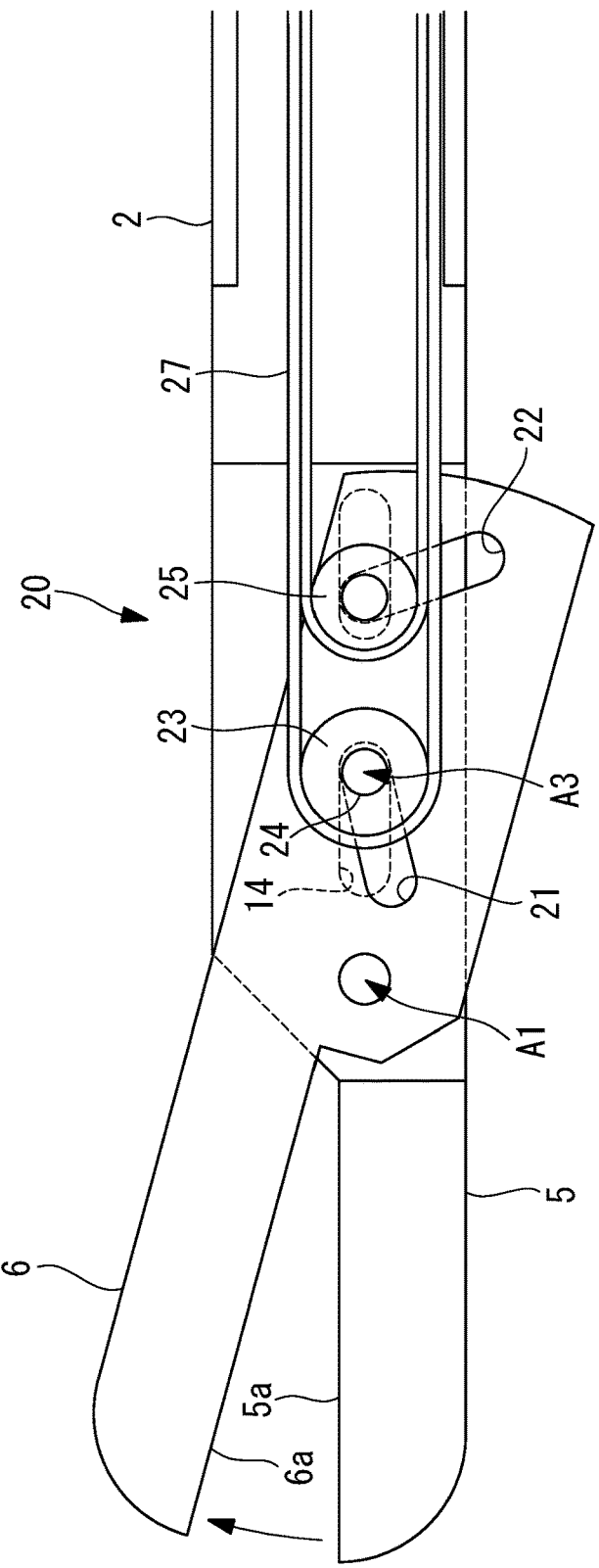
FIG. 15 is a longitudinal cross-sectional view showing a state in which the two gripping pieces of the gripping mechanism in FIG. 14 are open.

In this embodiment, although the first pulley 23 and the second pulley 25 are disposed so as to sandwich the longitudinal axis of the body portion 2 therebetween, alternatively, as shown in FIGS. 14 and 15, the first pulley 23 and the second pulley 25 may be disposed next to each other in the longitudinal direction on one side of the body portion 2.

In this case, it is possible to reduce the outer diameter of the gripping mechanism 20 by reducing the size of a space, in the radial direction of the body portion 2, required to dispose the two pulleys 23 and 25.

Next, a gripping mechanism 30 according to a fourth embodiment of the present invention will be described below with reference to the drawings.

In describing this embodiment, portions having the same configurations as the gripping mechanism 20 according to the third embodiment, described above, will be given the same reference signs, and descriptions thereof will be omitted.

In the gripping mechanism 30 according to this embodiment, as with the gripping mechanism 20 according to the third embodiment, the first gripping piece 5 and the second gripping piece 6 are individually supported at the distal end of the body portion 2 so as to be pivotable about the pivoting axis A1; however, the gripping mechanism 30 differs from the gripping mechanism 20 according to the third embodiment in that shafts 33 and 34 that support pulleys 31 and 32 in a pivotable manner are secured on the proximal-end side of the individual gripping pieces 5 and 6. In the figure, reference signs 35 and 36 are idlers.

Figure 16:
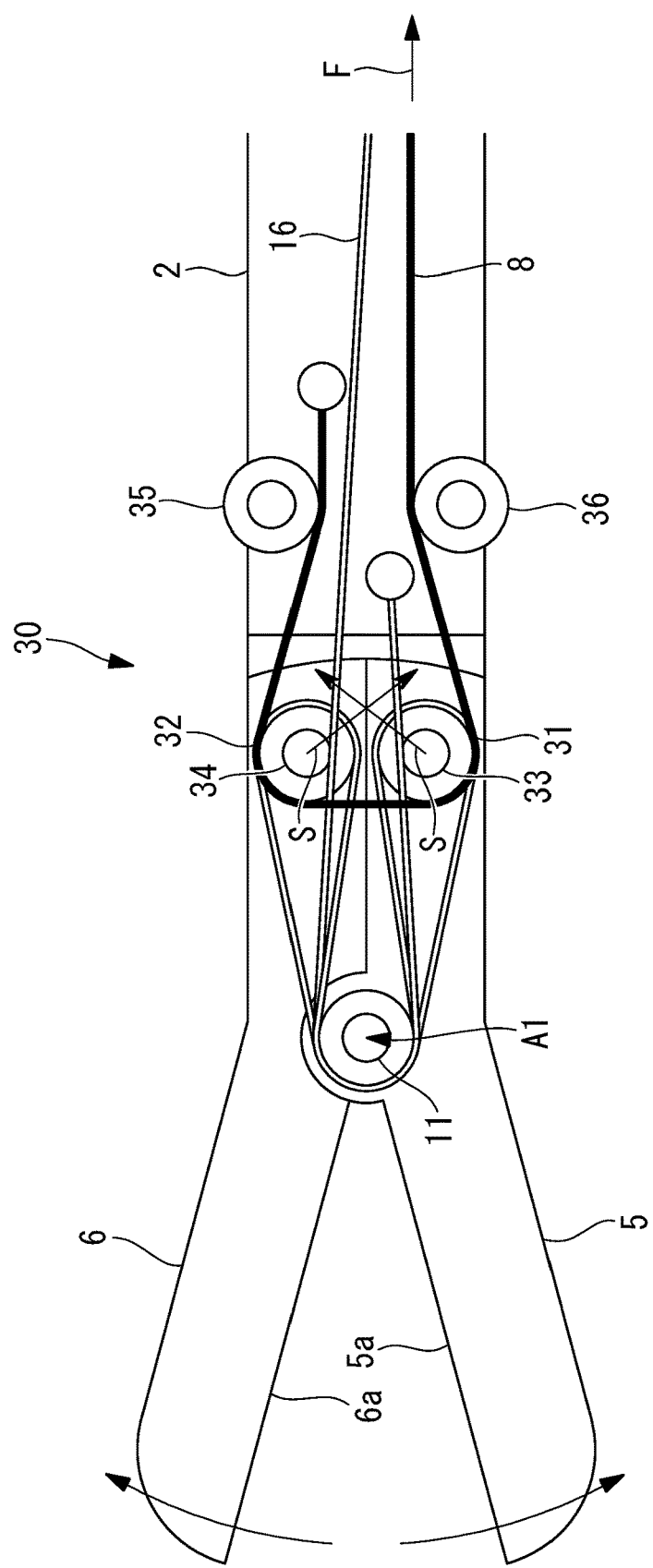
FIG. 16 is a longitudinal cross-sectional view showing a state in which two gripping pieces of a gripping mechanism according to a fourth embodiment of the present invention are open.

As shown in FIG. 16, the opening wire 8 being guided from the proximal end of the body portion 2 is wound around the pulleys 31 and 32 and is subsequently secured to the body portion 2 at the distal end thereof.

Figure 17:
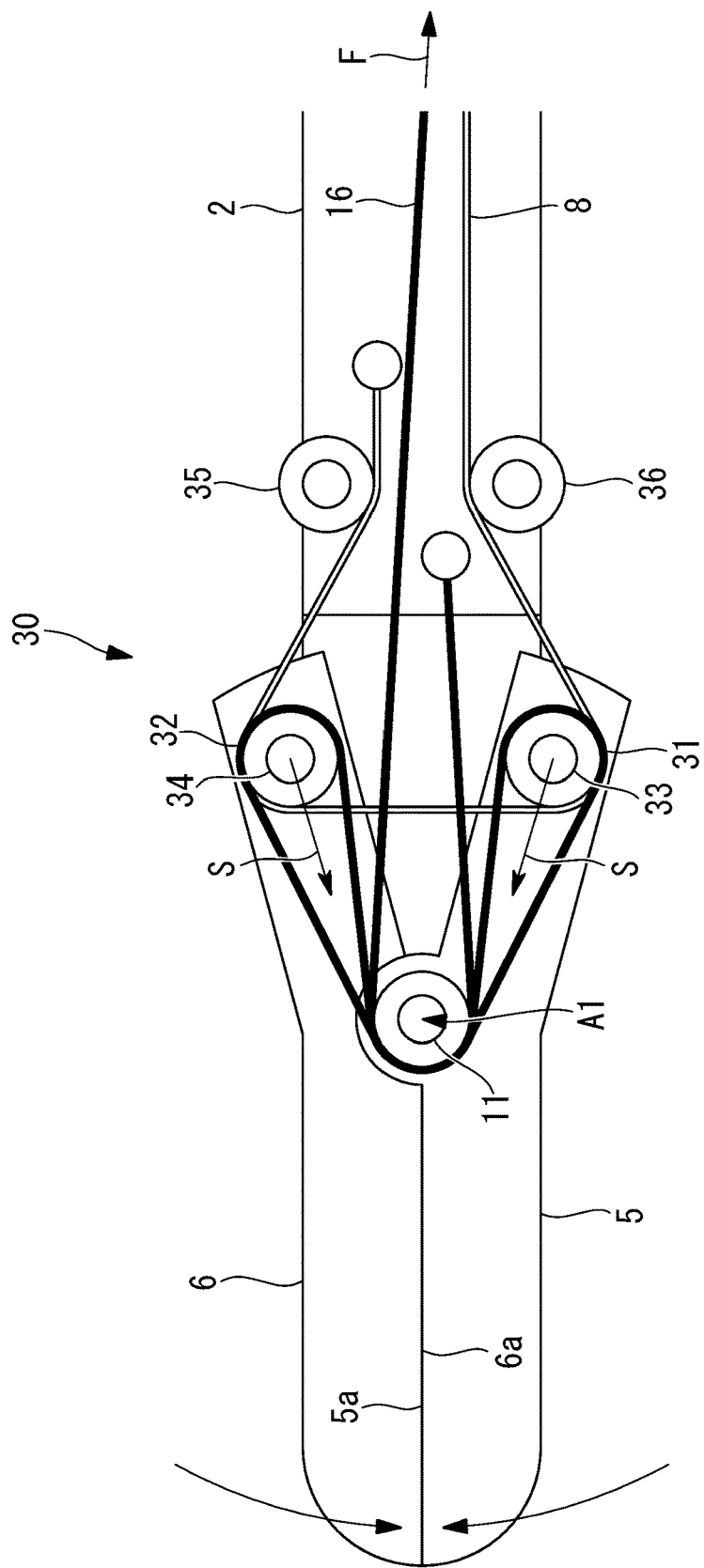
FIG. 17 is a longitudinal cross-sectional view in which the two gripping pieces of the gripping mechanism in FIG. 16 are closed.

As shown in FIG. 17, the closing wire 16 being guided from the proximal end of the body portion 2 is folded back by being wound around the return pulley 11 that is supported so as to be pivotable about the pivoting axis A1, is folded back by being wound around the pulley 31 provided in the first gripping piece 5, is once again folded back by the return pulley 11, is folded back by being wound around the pulley 31 provided in the second gripping piece 6, and is subsequently secured to the body portion 2 at the distal end thereof.

With the thus-configured gripping mechanism 30 according to this embodiment, because the pulleys 31 and 32 are pulled with the resultant force S having a greater magnitude than those of the pulling forces F applied to the proximal ends of the opening wire 8 and closing wire 16, there is an advantage in that, just by applying small pulling forces F, it is possible to open/close the first gripping piece 5 and the second gripping piece 6 with a large resultant force S.

Although the gripper 1 provided with the driving portion 4 having a motor has been described as an example, a unit with which the pulling force F is manually exerted on the wire 8 or the like may be employed as the driving portion 4.

As a result, the following aspects of the present invention are derived from the above-described embodiments.

A first aspect of the present invention is a gripping mechanism comprising: two gripping pieces that are pivoted relative to each other about a pivoting axis; a gripper main body that supports at least one of the gripping pieces so as to pivot at a distal-end portion thereof; a pulley that is supported so as to rotate about a rotation axis that is parallel to the pivoting axis; and an opening wire that is wound around the pulley, that has one end thereof secured to one of the gripping pieces or the gripper main body, and that causes, with a pulling force applied to the other end thereof, tensile forces that cause the rotation axis to be moved in one direction to act on two sides of the pulley, with the rotation axis being interposed therebetween, wherein the pulley is disposed so that a resultant force of the tensile forces in the opening wire that acts on the rotation axis becomes greater than the pulling force, and so that a moment that causes the gripping pieces to be pivoted in the directions in which the gripping pieces are opened relative to each other is generated.

With this aspect, when the pulling force is applied to the other end of the opening wire, tensile forces that are equal to the pulling force are generated in the opening wire, and the resultant force of the tensile forces acting in the longitudinal direction in the portions of the opening wire on the two sides sandwiching the rotation axis therebetween is applied to the pulley around which the wire is wound. As a result of this resultant force generating a moment about the pivoting axis in the opening direction of at least one of the gripping pieces, the two gripping pieces are pivoted in the direction in which the two gripping pieces are opened relative to each other.

In this case, with this aspect, the pulley is disposed so that the resultant force that acts on the pulley becomes greater than the pulling force. In other words, by disposing the pulley so that the relative angle of the wire that extends in the tangential directions of the pulley on the two sides thereof between which the rotation axis is sandwiched becomes less than 120°, it is possible to apply an amplified force as compared to the case in which the pulling force is directly applied at the position of the rotation axis without involving the pulley, and thus, it is possible to cause, with a greater force, the two gripping pieces to be pivoted in the direction in which the two gripping pieces are opened relative to each other.

The above-described aspect may further comprise a closing wire that is wound around the pulley, that has one end thereof secured to the gripper main body, and that causes, with a closing pulling force applied to the other end thereof, tensile forces that cause the rotation axis to be moved in an opposite direction from the direction of the movement caused by the opening wire with a resultant force that is greater than the closing pulling force to act on the two sides of the pulley with the rotation axis interposed therebetween.

By doing so, when the closing pulling force is applied to the other end of the closing wire, the resultant force of the tensile forces acting on the closing wire that extends on the two sides of the pulley around which the closing wire is wound acts on the rotation axis. Because the resultant force at this time is directed in the opposite direction from the direction of the movement caused by the opening wire and becomes greater than the closing pulling force, it is possible to cause, with a greater force, the two gripping pieces to pivot relative to each other in the closing direction by amplifying the applied closing pulling force.

The above-described aspect may further comprise a return portion that folds back the opening wire wound around the pulley toward the proximal end of the gripper main body.

By doing so, it is possible to apply the pulling force to the other end of the opening wire, which is folded back by the return portion and disposed on the proximal-end side of the gripper main body, and thus, it is possible to reduce the diameter of the gripping mechanism.

In the above-described aspect, the return portion may be disposed coaxially with the pivoting axis.

By doing so, by using the pivoting axis also as an axis at which the opening wire is folded back without providing another axis for this purpose, an efficient use of a space is achieved, and thus, it is possible to reduce the diameter of the gripping mechanism.

In the above-described aspect, the pulley may be supported so as to move, by means of the tensile forces in the opening wire, in a direction in which a distance between a straight line that passes through the rotation axis and that extends in the direction of the resultant force and the pivoting axis increases.

By doing so, because the moment generated by the resultant force is proportional to the distance between the straight line that passes through the rotation axis of the pulley and that extends in the direction of the resultant force and the pivoting axis, by moving the pulley in the direction in which said distance increases, it is possible to further amplify the moment in the opening direction that acts on at least one of the gripping pieces.

The above-described aspect may further comprise: a first elongated hole provided in the gripper main body so as to extend from the distal end to the proximal end thereof; and a second elongated hole provided in at least one of the gripping pieces so as to extend in a direction that is inclined in one direction with respect to the first elongated hole along a plane that is orthogonal to the pivoting axis, wherein the rotation axis is provided so as to move along the longitudinal direction of the first elongated hole and the second elongated hole.

By doing so, as a result of the resultant force component that is orthogonal to the longitudinal axis of the second elongated hole pushing the second elongated hole in the direction that is orthogonal to said longitudinal axis, a moment is generated about the pivoting axis, and thus, the second gripping piece is pivoted relative to the first gripping piece. Because the resultant force formed by amplifying the pulling force is used, it is possible to cause, even with a small pulling force, the second gripping piece to be pivoted.

Another aspect of the present invention is a gripping mechanism comprising: two gripping pieces that are pivoted about a pivoting axis relative to each other; a gripper main body that supports at least one of the gripping pieces so as to pivot at a distal-end portion thereof; a first pulley and a second pulley that are supported so as to individually rotate about a first rotation axis and a second rotation axis that are parallel to the pivoting axis; an opening wire that is wound around the first pulley, that has one end thereof secured to one of the gripping pieces or the gripper main body, and that causes, with a first pulling force applied to the other end thereof, tensile forces that cause the first rotation axis to be moved in one direction to act on two sides of the first pulley, with the first rotation axis being interposed therebetween; and a closing wire that is wound around the second pulley, that has one end thereof secured to the gripper main body, and that causes, with a second pulling force applied to the other end thereof, tensile forces that cause the second rotation axis to be moved in the other direction to act on two sides of the second pulley, with the second rotation axis being interposed therebetween, wherein the first pulley is disposed so that a resultant force of the tensile forces in the opening wire that act on the first rotation axis becomes greater than the first pulling force, and so that a moment that causes the gripping pieces to be pivoted in the directions in which the gripping pieces are opened relative to each other is generated, and the second pulley is disposed so that a resultant force of the tensile forces in the opening wire that acts on the second rotation axis becomes greater than the second pulling force, and so that a moment that causes the gripping pieces to be pivoted in the directions in which the gripping pieces are closed relative to each other is generated.

With this aspect, when the first pulling force is applied to the proximal end of the opening wire wound around the first pulley, the first pulling force is amplified and causes the two gripping pieces to be pivoted in the directions in which the two gripping pieces are opened relative to each other, and, when the second pulling force is applied to the proximal end of the closing wire wound around the second pulley, the second pulling force is amplified and causes the two gripping pieces to be pivoted in the directions in which the two gripping pieces are closed relative to each other. When opening as well as closing the gripping pieces, it is possible to cause the gripping pieces to be pivoted with a force that is greater than the applied pulling force.

The above-described aspect may further comprise: a first elongated hole provided in the gripper main body so as to extend from the distal end to the proximal end thereof; and a second elongated hole and a third elongated hole provided in at least one of the gripping pieces so as to extend in intersecting directions that are inclined in opposite directions with respect to the first elongated hole along a plane that is orthogonal to the pivoting axis, the first rotation axis is provided so as to move along the longitudinal direction of the first elongated hole and the second elongated hole, and the second rotation axis is provided so as to move along the longitudinal direction of the first elongated hole and the third elongated hole.

By doing so, when the first pulling force is applied to the other end of the opening wire, a force that is greater than the first pulling force acts on the first rotation axis of the first pulley around which the opening wire is wound, and the first rotation axis is moved in one direction along the longitudinal direction of the first elongated hole and the second elongated hole. Because the second elongated hole extends in one direction in an inclined manner with respect to the first elongated hole along the plane that is orthogonal to the pivoting axis, the gripping piece in which the second elongated hole is provided is caused to be pivoted about the pivoting axis in the opening direction in association of the movement of the first rotation axis.

On the other hand, when the second pulling force is applied to the other end of the closing wire, a force that is greater than the second pulling force acts on the second rotation axis of the second pulley around which the closing wire is wound, and the second rotation axis is moved in one direction along the longitudinal direction of the first elongated hole and the third elongated hole. Because the third elongated hole extends in the opposite direction from the second elongated hole in an inclined manner with respect to the first elongated hole along the plane that is orthogonal to the pivoting axis, the gripping piece in which the third elongated hole is provided is caused to be pivoted with respect to the gripper main body in the closing direction in association with the movement of the second rotation axis.

By doing so, it is possible to open/close the two gripping pieces with a smaller pulling force.

In the above-described aspect, the two gripping pieces may be provided so as to individually pivot with respect to the gripper main body, and the pulley may be disposed so as to cause the two gripping pieces to be pivoted.

By doing so, when, by applying the pulling force to the opening wire, the pulley is pulled with a force that is greater than the applied pulling force, the two gripping pieces are pivoted with respect to the gripper main body. By doing so, it is possible to open the two gripping pieces with a smaller pulling force.

Another aspect of the present invention is a gripper provided with: any one of the above-described gripping mechanisms; and a driving portion that is connected to the gripping mechanism and that generates the pulling force.

With this aspect, as a result of generating the pulling force by operating the driving portion, it is possible to open the two gripping pieces relative to each other, with a smaller pulling force.

REFERENCE SIGNS LIST 1 gripper
2 body portion (gripper main body)
3, 13, 20, 30 gripping mechanism
4 driving portion
5 first gripping piece (gripping piece)
6 second gripping piece (gripping piece)
7, 31, 32 pulley
8, 27 wire (opening wire)
11 return pulley (return portion)
14 first elongated hole
15, 21 second elongated hole
16, 28 wire (closing wire)
22 third elongated hole
23 first pulley
25 second pulley
A1 pivoting axis
A2 rotation axis
A3 first rotation axis
A4 second rotation axis
S resultant force

The invention claimed is:

1. A gripping mechanism comprising:
two gripping pieces that are pivoted relative to each other about a pivoting axis;
a gripper main body that supports at least one of the gripping pieces so as to pivot at a distal-end portion thereof;
a pulley that is supported so as to rotate about a rotation axis that is parallel to the pivoting axis; and
an opening wire that is wound around the pulley, that has one end thereof secured to one of the gripping pieces or the gripper main body, and that causes, with a pulling force applied to the other end thereof, tensile forces that cause the rotation axis to be moved in one direction to act on two sides of the pulley, with the rotation axis being interposed therebetween,
wherein the pulley is disposed so that a resultant force of the tensile forces in the opening wire that acts on the rotation axis becomes greater than the pulling force, and so that a moment that causes the gripping pieces to be pivoted in the directions in which the gripping pieces are opened relative to each other is generated.

2. A gripping mechanism according to claim 1, further comprising:
a closing wire that is wound around the pulley, that has one end thereof secured to the gripper main body, and that causes, with a closing pulling force applied to the other end thereof, tensile forces that cause the rotation axis to be moved in an opposite direction from the direction of the movement caused by the opening wire with a resultant force that is greater than the closing pulling force to act on the two sides of the pulley with the rotation axis interposed therebetween.

3. A gripping mechanism according to claim 1, further comprising:
a return portion that folds back the opening wire wound around the pulley toward the proximal end of the gripper main body.

4. A gripper mechanism according to claim 3, wherein the return portion is disposed coaxially with the pivoting axis.

5. A gripper mechanism according to claim 1, wherein the pulley is supported so as to move, by means of the tensile forces in the opening wire, in a direction in which a distance between a straight line that passes through the rotation axis and that extends in the direction of the resultant force and the pivoting axis increases.

6. A gripping mechanism according to claim 1, further comprising:
a first elongated hole provided in the gripper main body so as to extend from the distal end to the proximal end thereof; and
a second elongated hole provided in at least one of the gripping pieces so as to extend in a direction that is inclined in one direction with respect to the first elongated hole along a plane that is orthogonal to the pivoting axis,
wherein the rotation axis is provided so as to move along the longitudinal direction of the first elongated hole and the second elongated hole.

7. A gripping mechanism according to claim 1,
wherein the two gripping pieces are provided so as to individually pivot with respect to the gripper main body, and the pulley is disposed so as to cause the two gripping pieces to be pivoted.

8. A gripper comprising:

a gripping mechanism according to claim 1; and a driving portion that is connected to the gripping mechanism and that is configured to generate the pulling force.

9. A gripping mechanism comprising:

two gripping pieces that are pivoted about a pivoting axis relative to each other;

a gripper main body that supports at least one of the gripping pieces so as to pivot at a distal-end portion thereof;

a first pulley and a second pulley that are supported so as to individually rotate about a first rotation axis and a second rotation axis that are parallel to the pivoting axis;

an opening wire that is wound around the first pulley, that has one end thereof secured to one of the gripping pieces or the gripper main body, and that causes, with a first pulling force applied to the other end thereof, tensile forces that cause the first rotation axis to be moved in one direction to act on two sides of the first pulley, with the first rotation axis being interposed therebetween; and a closing wire that is wound around the second pulley, that has one end thereof secured to the gripper main body, and that causes, with a second pulling force applied to the other end thereof, tensile forces that cause the second rotation axis to be moved in the other direction to act on two sides of the second pulley, with the second rotation axis being interposed therebetween, wherein the first pulley is disposed so that a resultant force of the tensile forces in the opening wire that act on the first rotation axis becomes greater than the first pulling force, and so that a moment that causes the gripping pieces to be pivoted in the directions in which the gripping pieces are opened relative to each other is generated, and the second pulley is disposed so that a resultant force of the tensile forces in the opening wire that acts on the second rotation axis becomes greater than the second pulling force, and so that a moment that causes the gripping pieces to be pivoted in the directions in which the gripping pieces are closed relative to each other is generated.

10. A gripping mechanism according to claim 9, further comprising:

a first elongated hole provided in the gripper main body so as to extend from the distal end to the proximal end thereof; and a second elongated hole and a third elongated hole provided in at least one of the gripping pieces so as to extend in intersecting directions that are inclined in opposite directions with respect to the first elongated hole along a plane that is orthogonal to the pivoting axis, the first rotation axis is provided so as to be movable along the longitudinal direction of the first elongated hole and the second elongated hole, and the second rotation axis is provided so as to move along the longitudinal direction of the first elongated hole and the third elongated hole.

11. A gripper comprising:

a gripping mechanism according to claim 9; and a driving portion that is connected to the gripping mechanism and that is configured to generate the pulling force.

\* \* \* \* \*